United States Patent [19]

Förster et al.

[11] Patent Number: 4,596,594
[45] Date of Patent: Jun. 24, 1986

[54] SILICON-CONTAINING PHENOXYPROPIONIC ACID DERIVATIVES AND HERBICIDAL USE

[75] Inventors: Heinz Förster, Wuppertal; Ludwig Eue, Leverkusen; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 774,115

[22] Filed: Sep. 9, 1985

[30] Foreign Application Priority Data

Sep. 12, 1984 [DE] Fed. Rep. of Germany ....... 3433390

[51] Int. Cl.$^4$ .......................... A01N 55/00; C07F 7/10
[52] U.S. Cl. .......................................... 71/88; 71/90; 71/94; 546/14; 548/110
[58] Field of Search .............. 546/14; 548/110; 71/88, 71/90, 94

[56] References Cited

U.S. PATENT DOCUMENTS 4,509,971  4/1985  Förster et al. ...................... 71/90

FOREIGN PATENT DOCUMENTS 2640730  3/1978  Fed. Rep. of Germany .

Primary Examiner—Richard L. Raymond
Attorney, Agent, or Firm—Sprung Horn Kramer & Woods

[57] ABSTRACT

Herbicidally active novel phenoxypropionic acid derivatives of the formula

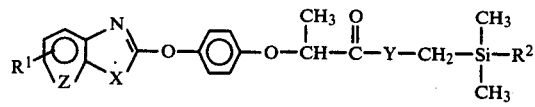

in which
X represents oxygen or sulphur,
Y represents oxygen, sulphur or the grouping of the formula NR,
R represents hydrogen or alkyl with 1 to 6 carbon atoms,
Z represents nitrogen or the CH group,
R$^1$ represents hydrogen or halogen and
R$^2$ represents alkyl with 1 to 6 carbon atoms.

11 Claims, No Drawings

SILICON-CONTAINING PHENOXYPROPIONIC ACID DERIVATIVES AND HERBICIDAL USE

The invention relates to new phenoxypropionic acid derivatives, several processes for their preparation and their use as herbicides.

It is already known that numerous phenoxypropionic acid derivatives have herbicidal properties (compare DE-OS (German Published Specification) No. 2,640,730). Thus, for example, ethyl 2-{4-[(6-chloro-2-benzothiazolyl)-oxy]-phenoxy}-propionate and ethyl 2-{4-[(6-chloro-2-benzoxazolyl)-oxy]-phenoxy}-propionate can be used for combating weeds. The action of these substances is good, but some weeds are not always completely affected when low amounts are applied. In addition, the selectivity in some cases leaves something to be desired.

New phenoxypropionic acid derivatives of the formula

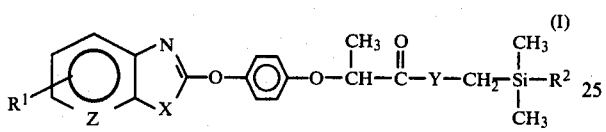

in which
X represents oxygen or sulphur,
Y represents oxygen, sulphur or the grouping of the formula NR,
wherein
R represents hydrogen or alkyl with 1 to 6 carbon atoms,
Z represents nitrogen or the CH group,
$R^1$ represents hydrogen or halogen and
$R^2$ represents alkyl with 1 to 6 carbon atoms, have now been found.

The phenoxypropionic acid derivatives of the formula (I) contain at least one asymmetrically substituted carbon atom and can therefore exist in various enantiomeric forms. The invention relates both to the possible individual isomers and to mixtures of these isomers.

It has furthermore been found that phenoxypropionic acid derivatives of the formula (I) are obtained by a process in which (a) propionic acid derivatives of the formula

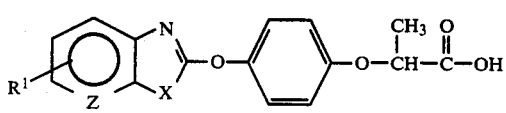

in which
$R^1$, X and Z have the abovementioned meaning, are reacted with silyl chlorides of the formula

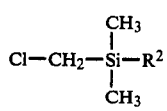

in which
$R^2$ has the abovementioned meaning, if appropriate in the presence of an acid-binding agent and if appropriate in the presence of a diluent, or (b) phenoxypropionyl chlorides of the formula

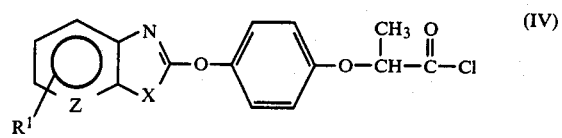

in which
$R^1$, X and Z have the abovementioned meaning, are reacted with compounds of the formula

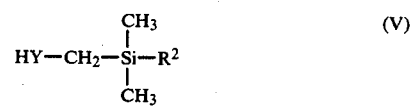

in which
$R^2$ and Y have the abovementioned meaning, if appropriate in the presence of an acid-binding agent and if appropriate in the presence of a diluent, or (c) heterocyclic compounds of the formula

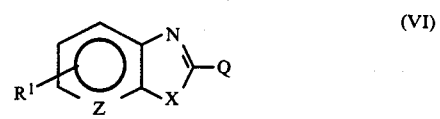

in which
$R^1$, X and Z have the abovementioned meaning and
Q represents halogen, methylsulphonyl, ethylsulphonyl or tosyl,
are reacted with hydroquinone derivatives of the formula

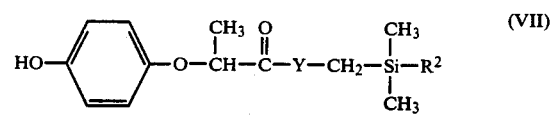

in which
$R^2$ and Y have the abovementioned meaning,
if appropriate in the presence of an acid-binding agent and if appropriate in the presence of a diluent.

Finally, it has been found that the new phenoxypropionic acid derivatives of the formula (I) are distinguished by an outstanding herbicidal activity.

Surprisingly, the phenoxypropionic acid derivatives of the formula (I) according to the invention have substantially better herbicidal properties than ethyl 2-{4-[(6-chloro-2-benzothiazolyl)-oxy]-phenoxy}-propionate and ethyl 2-{4-[(6-chloro-2-benzoxazolyl)-oxy]-phenoxy}-propionate, which are structurally the most similar of the active compounds of the same type of action which are already known.

Formula (I) provides a general definition of the phenoxypropionic acid derivatives according to the invention. In this formula,
X represents oxygen or sulphur,
Y preferably represents oxygen, sulphur or the grouping of the formula NR,
wherein
R preferably represents hydrogen or alkyl with 1 to 4 carbon atoms,
Z preferably represents nitrogen or the CH group,
$R^1$ preferably represents hydrogen, fluorine, chlorine or bromine and $R^2$ preferably represents alkyl with 1 to 4 carbon atoms.

Particularly preferred compounds of the formula (I) are those in which

X represents oxygen or sulphur,

Y represents oxygen, sulphur or the grouping of the formula NR, wherein

R represents hydrogen, methyl, ethyl, n-propyl or isopropyl,

Z represents nitrogen or the CH group, $R^1$ represents hydrogen, fluorine or chlorine and $R^2$ represents methyl, ethyl, n-propyl or n-butyl.

Finally, another group of particularly preferred compounds according to the invention are those phenoxypropionic acid derivatives of the formula (I) in which the asymmetrically substituted carbon atom of the propionic acid unit has the R-configuration and the radicals X, Y, Z, $R^1$ and $R^2$ have the abovementioned particularly preferred meanings. The substances in question can be characterized by the formula

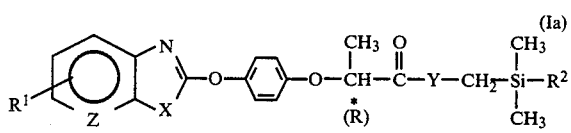

In this formula (Ia), the asymmetrically substituted carbon atom is identified by an (*).

The compounds listed by way of their formulae in the following table may be mentioned as examples of phenoxypropionic acid derivatives of the formula (I):

TABLE 1

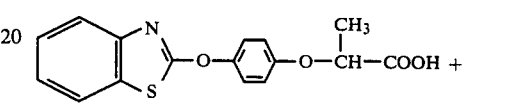

| $R^1$ | Z | X | Y | $R^2$ |
|---|---|---|---|---|
| H | CH | O | O | $CH_3$ |
| 6-Cl | CH | O | O | $CH_3$ |
| H | N | O | O | $CH_3$ |
| 6-Cl | N | O | O | $CH_3$ |
| H | CH | S | O | $CH_3$ |
| 6-Cl | CH | S | O | $CH_3$ |
| H | N | S | O | $CH_3$ |
| H | N | S | O | $C_2H_5$ |
| 6-Cl | N | S | O | $CH_3$ |
| H | CH | O | O | $C_2H_5$ |
| 6-Cl | CH | O | O | $C_2H_5$ |
| H | CH | O | O | $n-C_3H_7$ |
| 6-Cl | CH | O | O | $n-C_3H_7$ |
| H | CH | O | O | $n-C_4H_9$ |
| 6-Cl | CH | O | O | $n-C_4H_9$ |
| 6-Cl | CH | O | NH | $CH_3$ |
| 6-Cl | CH | O | NH | $C_2H_5$ |
| 6-Cl | CH | O | NH | $n-C_3H_7$ |
| 6-Cl | CH | O | NH | $n-C_4H_9$ |
| 6-Cl | CH | O | $NCH_3$ | $CH_3$ |
| 6-Cl | CH | O | $NCH_3$ | $C_2H_5$ |
| 6-Cl | CH | O | $NCH_3$ | $n-C_3H_7$ |
| 6-Cl | CH | O | $NCH_3$ | $n-C_4H_9$ |
| 6-Cl | CH | S | NH | $CH_3$ |
| 6-Cl | CH | S | NH | $C_2H_5$ |
| 6-Cl | CH | S | NH | $n-C_4H_9$ |
| 6-Cl | CH | S | $NCH_3$ | $CH_3$ |
| 6-Cl | CH | S | $NCH_3$ | $n-C_3H_7$ |
| 6-Cl | CH | S | S | $C_2H_5$ |
| 6-Cl | CH | S | S | $n-C_4H_9$ |
| 6-Cl | CH | O | S | $CH_3$ |
| 6-Cl | CH | O | S | $C_2H_5$ |
| 6-Cl | CH | O | S | $n-C_3H_7$ |

TABLE 1-continued

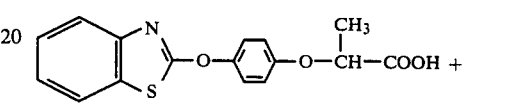

| $R^1$ | Z | X | Y | $R^2$ |
|---|---|---|---|---|
| 6-Cl | CH | O | S | $n-C_4H_9$ |

If 2-{4-[(2-benzothiazolyl)-oxy]-phenoxy}-propionic acid and chloromethyl-trimethylsilane are used as starting substances, the course of process (a) according to the invention can be represented by the following equation:

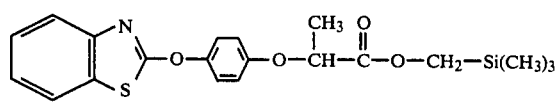

If 2-{4-[(6-chloro-2-benzoxazolyl)-oxy]-phenoxy}-propionyl chloride and (trimethylsilylmethyl)-mercaptan are used as starting substances, the course of process (b) according to the invention can be represented by the following equation:

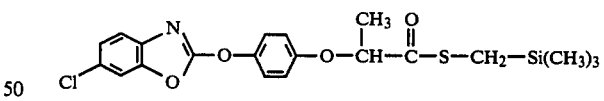

If 2-chloro-benzothiazole and trimethylsilylmethyl 2-(4-hydroxyphenoxy)-propionate are used as starting substances, the course of process (c) according to the invention can be represented by the following equation:

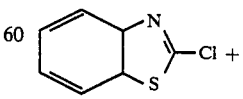
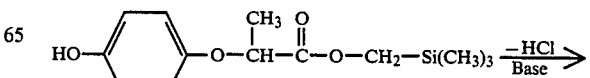

-continued

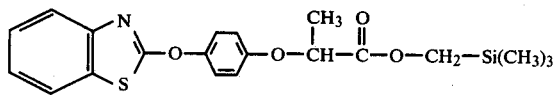

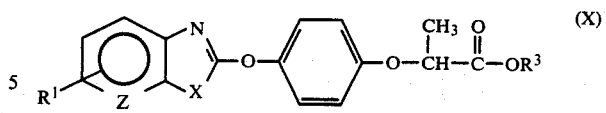

Formula (II) provides a definition of the propionic acid derivatives required as starting substances in process (a) according to the invention. In this formula, $R^1$, X and Z preferably have those meanings which have already been mentioned as preferred for these radicals in connection with the description of the substances of the formula (I) according to the invention.

The propionic acid derivatives of the formula (II) are known or can be prepared in a simple manner by known processes (compare DE-OS (German Published Specification) No. 2,640,730, EP-OS (European Published Specification) No. 0,075,840 and EP-OS (European Published Specification) No. 0,002,800).

Optically active R- or S-propionic acid derivatives of the formula (II) are required as starting substances in carrying out process (a) according to the invention for the preparation of R- and S-enantiomers of the phenoxypropionic acid derivatives of the formula (Ia). These optically active propionic acid derivatives of the formula (II) are also known or can be prepared in a simple manner by processes which are known in principle (compare European Published Application No. 0,002,800).

R- and S-enantiomers of the propionic acid derivatives of the formula

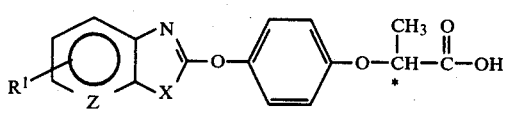

in which
  $R^1$, X and Z have the abovementioned meaning, are obtained by a process in which phenol derivatives of the formula

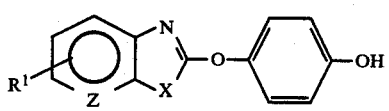

in which
  $R^1$, X and Z have the abovementioned meaning, are reacted with the S-enantiomers or R-enantiomers of propionic acid derivatives of the formula

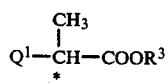

in which
  $Q^1$ represents chlorine, bromine, tosylate or mesylate and
  $R^3$ represents methyl or ethyl,
if appropriate in the presence of an acid acceptor, such as, for example, potassium carbonate, and if appropriate in the presence of a diluent, such as, for example, acetonitrile, at temperatures between 0° C. and 120° C., and the esters thereby formed, of the formula in which
  $R^1$, $R^3$, X and Z have the abovementioned meaning, are hydrolyzed with strong bases, such as, for example, sodium hydroxide, in the presence of a diluent, such as, for example, methanol, ethanol, benzene, toluene or xylene, if appropriate mixed with water, at temperatures between 20° C. and 140° C., and the products are then acidified with an acid, such as, for example, hydrochloric acid.

In the first stage of this reaction, Walden inversion takes place at the asymmetric carbon atom of the propionic acid unit. This results in formation of the R-enantiomers of the propionic acid derivatives of the formula (X) by reaction of phenol derivatives of the formula (VIII) with S-enantiomers of the propionic acid derivatives of the formula (IX). On the other hand, the S-enantiomers of the propionic acid derivatives of the formula (X) are formed by reaction of the R-enantiomers of phenol derivatives of the formula (VIII) with R-enantiomers of the propionic acid derivatives of the formula (IX).

Formula (III) provides a definition of the silyl chlorides furthermore required as starting substances in process (a) according to the invention. In this formula, $R^2$ preferably has those meanings which have already been mentioned as preferred for this radical in connection with the description of the substances of the formula (I) according to the invention.

The silyl chlorides of the formula (III) are known or can be prepared in a simple manner by known processes.

Formula (IV) provides a definition of the phenoxypropionyl chlorides required as starting substances in process (b) according to the invention. In this formula, $R^1$, X and Z preferably have those meanings which have already been mentioned as preferred for these radicals in connection with the description of the substances of the formula (I) according to the invention.

The phenoxypropionyl chlorides of the formula (IV) are known or can be prepared in a simple manner by known processes (compare DE-OS (German Published Specification) No. 2,640,730, EP-OS (European Published Specification) No. 0,075,840 and EP-OS (European Published Specification) No. 0,002,800). Thus, the phenoxypropionyl chlorides of the formula (IV) can be prepared from the corresponding propionic acid derivatives of the formula (II) by chlorination, for example with thionyl chloride, by customary methods.

Formula (V) provides a definition of the compounds furthermore required as starting substances in process (b) according to the invention. In this formula, $R^2$ and Y preferably have those meanings which have already been mentioned as preferred for these radicals in connection with the description of the substances of the formula (I) according to the invention.

The compounds of the formula (V) are known or can be prepared in a simple manner by known methods.

The R- or S-enantiomers of the phenoxypropionic acid chlorides of the formula (IV) are employed in carrying out process (b) according to the invention for the preparation of R- or S-enantiomers of the phenoxypropionic acid derivatives of the formula (I).

Formula (VI) provides a definition of the heterocyclic compounds required as starting substances in process (c) according to the invention. In this formula, $R^1$, Z and X preferably have those meanings which have already been mentioned as preferred for these radicals in connection with the description of the substances of the formula (I) according to the invention. Q preferably represents fluorine, chlorine, bromine, methylsulphonyl, ethylsulphonyl or tosyl.

The heterocyclic compounds of the formula (VI) are known (compare DE-OS (German Published Specification) No. 2,640,730, EP-OS (European Published Specification) No. 0,044,497 and EP-OS (European Published Specification) No. 0,075,840).

Formula (VII) provides a definition of the hydroquinone derivatives furthermore required as starting substances in process (c) according to the invention. In this formula, $R^2$ and Y preferably have those meanings which have already been mentioned as preferred for these radicals in connection with the description of the substances of the formula (I) according to the invention.

The hydroquinone derivatives of the formula (VII) are known in some cases (compare EP-OS (European Published Specification) No. 0,095,115). They can be prepared by a process in which, in a first stage, hydroquinone monobenzyl ether of the formula

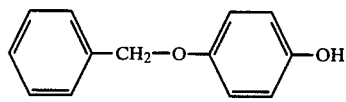    (XI)

is reacted with silyl compounds of the formula

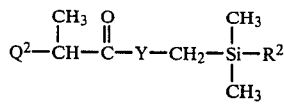    (XII)

in which

R² and Y have the abovementioned meaning and

Q² represents chlorine, bromine, tosylate or mesylate, if appropriate in the presence of an acid-binding agent and if appropriate in the presence of a polar diluent, such as, for example, dimethylformamide, dimethylsulphoxide, acetonitrile or methyl isobutyl ketone, at temperatures between 40° and 120° C., preferably between 60° and 100° C., and, in a second stage, the hydroquinone ethers formed, of the formula

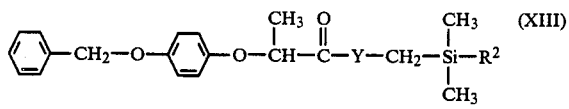    (XIII)

in which

R² and Y have the abovementioned meaning, are hydrogenated with hydrogen under a pressure of 10 bar to 100 bar in the presence of a catalyst, such as, for example, palladium on active charcoal, and in the presence of a diluent, such as, for example, ethyl acetate, at temperatures between 20° and 60° C.

Acid acceptors which can be employed in the first stage of this reaction are, preferably, all those acid-binding agents which are mentioned as preferred acid acceptors in connection with the description of processes (a) to (c) according to the invention (see below).

The hydroquinone monobenzyl ether of the formula (XI) required as the starting substance in the above process for the preparation of hydroquinone derivatives of the formula (VII) is known (compare J. Org. Chem. 39, (1974) 214–215).

The silyl compounds of the formula (XII) furthermore required as starting substances in the above process for the preparation of hydroquinone derivatives of the formula (VII) are known in some cases (compare EP-OS (European Published Specification) No. 0,095,115 and EP-OS (European Published Specification) No. 0,096,354). They can be prepared by a process in which propionic acid derivatives of the formula

    (XIV)

in which

Q³ represents chlorine, bromine, mesylate or tosylate, are reacted with compounds of the formula

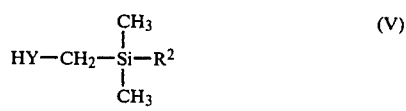    (V)

in which

R² and Y have the abovementioned meaning, if appropriate in the presence of an acid-binding agent and if appropriate in the presence of a diluent. The reaction conditions in this process correspond to those of process (b) according to the invention (see below).

The hydroquinone ethers of the formula (XIII) obtained as intermediates in the process for the preparation of hydroquinone derivatives of the formula (VII) are new.

The R- or S-enantiomers of the hydroquinone derivatives of the formula (VII) are employed in carrying out process (c) according to the invention to prepare R- or S-enantiomers of the phenoxypropionic acid derivatives of the formula (I). These optically active substances can also be synthesized by the process described above for the preparation of hydroquinone derivatives of the formula (VII), by using corresponding optically active silyl compounds of the formula (XII).

Processes (a), (b) and (c) according to the invention for the preparation of the new phenoxypropionic acid derivatives of the formula (I) are preferably carried out using diluents. Possible diluents are virtually all the inert organic solvents. These include, preferably, aliphatic and aromatic, optionally halogenated hydrocarbons, such as pentane, hexane, heptane, cyclohexane, petroleum ether, benzine, ligroin, benzene, toluene, xylene, methylene chloride, ethylene chloride, chloroform, carbon tetrachloride, chlorobenzene and o-dichlorobenzene, ethers, such as diethyl ether, dibutyl ether, glycol dimethyl ether, diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methylpyrrolidone, and dimethylsulphoxide, tetramethylene sulphone and hexamethylphosphoric acid triamide.

Acid-binding agents which can be employed both in processes (a) and (b) according to the invention and in process (c) are all the acid-binding agents which can usually be employed for such reactions. Preferred possible acid-binding agents are alkali metal hydroxides, such as, for example, sodium hydroxide and potassium hydroxide, alkaline earth metal hydroxides, for example calcium hydroxide, alkali metal carbonates and alcoholates, such as sodium carbonate, potassium carbonate, sodium methylate or ethylate and potassium methylate or ethylate, and furthermore aliphatic, aromatic or heterocyclic amines, for example triethylamine, trimethylamine, dimethylaniline, dimethylbenzylamine, pyridine, 1,5-diaza-bicyclo-[4.3.0]-non-5-ene (DBN) and 1,8-diazabicyclo-[5.4.0]-undec-7-ene (DBU).

The reaction temperatures can be varied within a substantial range both in process (a) according to the invention and in processes (b) and (c). In general, the reaction is in each case carried out at temperatures between $-20°$ C. and $+160°$ C., preferably between $0°$ C. and $140°$ C.

Processes (a), (b) and (c) according to the invention are in general carried out under normal pressure. However, it is also possible to carry out the processes under increased or reduced pressure.

For carrying out processes (a), (b) and (c) according to the invention, in each case the required starting substances are in general employed in approximately equimolar amounts. However, it is also possible for one of the two particular components employed to be used in a larger excess. The reactions are in general carried out in a suitable diluent in the presence of an acid acceptor, and the reaction mixture is stirred at the particular required temperature for several hours. Working up in processes (a), (b) and (c) according to the invention is in each case effected by customary methods.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiara, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention are particularly suitable for selectively combating weeds in cereals and rice. In particular, they have a very good action against gramineous weeds.

The active compounds can be converted to the customary formulations, such as solutions, emulsions, wettable powders, suspensions, powders, dusting agents, soluble powders, granules, suspension-emulsion concentrates, natural and synthetic materials impregnated with active compound, and very fine capsules in polymeric substances.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95% by weight of active compound, preferably between 0.5 and 90%.

The active compounds according to the invention, as such or in the form of their formulations, can also be used, for combating weeds, as mixtures with known herbicides, finished formulations or tank mixes being possible.

Known herbicides, such as, for example, N-(2-benzothiazolyl)-N,N'-dimethyl-urea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5(4H)-one, 4-amino-6-(1,1-dimethylethyl)-3-ethylthio-1,2,4-triazin-5(4H)-one, 1-amino-6-ethylthio-3-(2,2-dimethylpropyl)-1,3,5-triazine-2,4-(1H,3H)-dione, 4-amino-3-methyl-6-phenyl-1,2,4-triazin-5(4H)-one; 2-chloro-4-ethylamino-6-isopropylamino-1,3,5-triazine, the R-enantiomer of (trimethylsilyl)-methyl 2-[4-(3,5-dichloropyridin-2-oxy)-phenoxy]-propionate, the R-enantiomer of (2-benzyloxy)-ethyl 2-[4-(3,5-dichloropyridyl-2-oxy)-phenoxy]-propionate, 2,4-dichlorophenoxyacetic acid, 2-(2,4-dichlorophenoxy)-propionic acid, 4-chloro-2-methylphenoxy-acetic acid, 2-(2-methyl-3-chloro-phenoxy)-propionic acid, 3,5-diiodo-4-hydroxy-benzonitrile, 3,5-dibromo-4-hydroxy-benzonitrile and diphenyl ethers and phenylpyridazines, such as, for example, pyridates can be used for the mixtures. Surprisingly, some mixtures also show a synergistic action.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 15 kg of active compound per hectare of soil surface, preferably between 0.05 and 10 kg per ha.

The preparation and use of the active compounds according to the invention can be seen from the following examples.

PREPARATION EXAMPLES

Example 1

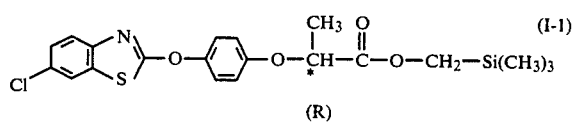

2.9 g of potassium carbonate are added to a solution of 6.2 g (0.179 mole) of the R-enantiomer of 2-{4-[(6-chloro-2-benzothiazolyl)-oxy]-phenoxy}-propionic acid in 20 ml of dimethylformamide. After the mixture has been stirred at 50° C. for 15 minutes, 2.7 g (0.021 mole) of chloromethyltrimethylsilane are added dropwise at this temperature. The mixture is then subsequently stirred at 80° C. for 2 hours. It is then worked up by stripping off the solvent under reduced pressure, adding water to the residue and extracting the resulting oily product with 100 ml of toluene. The organic phase is washed successively with aqueous sodium carbonate solution and with water, dried and concentrated under reduced pressure. 7 g (89% of theory) of the R-enantiomer of trimethylsilyl-methyl 2-{4-[(6-chloro-2-benzothiazolyl)-oxy]-phenoxy}-propionate are obtained in this manner in the form of a viscous oil.

Refractive index: $n_D^{20} = 1.5771$.

Optical rotation: $[\alpha]_D^{24} = +12.20°$ (1 molar solution in chloroform; cell length of 10 cm).

Example 2

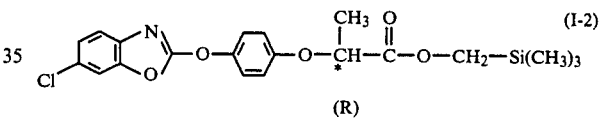

A mixture of 6.7 g (0.025 mole) of the R-enantiomer of trimethylsilyl-methyl 2-(4-hydroxy-phenoxy)-propionate, 0.9 g of calcium hydroxide and 10 ml of dimethylsulphoxide is heated at 40° C. A solution of 4.7 g (0.025 mole) of 2,6-dichlorobenzoxazole in 15 ml of dimethylsulphoxide is slowly added dropwise at this temperature, with stirring. The reaction mixture is subsequently stirred at 40° C. for 2 hours and at room temperature for 16 hours. Working up is then carried out by pouring the reaction mixture into water, extracting the resulting oily product with cyclohexane, washing the organic phase successively with dilute aqueous sodium hydroxide solution and water, rendering it weakly acidic with glacial acetic acid and then drying it and concentrating it under reduced pressure. 9.3 g (88.6% of theory) of the R-enantiomer of trimethylsilyl-methyl 2-{4-[(6-chloro-2-benzoxazolyl)-oxy]-phenoxy}-propionate are obtained in this manner in the form of crystals.

Melting point: 68° C.

Optical rotation: $[\alpha]_D^{24} = +10.3°$ (1 molar solution in chloroform; cell length of 10 cm).

Example 3

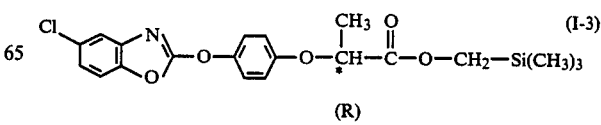

The compound of the formula (I-3) is also prepared by the method described in Example 2.

Refractive index: $n_D^{20} = 1.5204$

Optical rotation: $[\alpha]_D^{24} = +11.6°$ (1 molar solution in chloroform; cell length of 10 cm).

Example 4

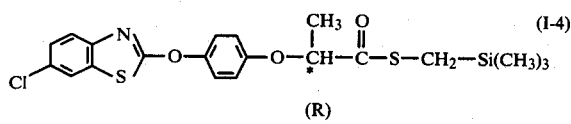

A solution of 4.9 g (0.013 mole) of the R-enantiomer of 2-{4-[(6-chloro-2-benzothiazolyl)-oxy]-phenoxy}-propionyl chloride in 10 ml of toluene is added dropwise to a mixture of 1.56 g (0.013 mole) of (trimethylsilylmethyl)-mercaptan, 1.6 g (0.016 mole) of triethylamine and 20 ml of toluene at 0° C., with stirring. The mixture is subsequently stirred at temperatures between 0° C. and 5° C. for 3 hours and is then worked up by a procedure in which the reaction mixture is diluted with water, the oily product obtained is extracted with toluene and the organic phase is washed rapidly with 5% strength aqueous sodium hydroxide solution and then washed with dilute acetic acid and water and, after drying, is concentrated by stripping off the diluent under reduced pressure. 4.5 g (77% of theory) of the R-enantiomer of trimethylsilyl-methyl 2-{4-[(6-chloro-2-benzothiazolyl)-oxy]-phenoxy}-thiopropionate are obtained in this manner. Melting point: 90° C.

$[\alpha]_D^{24} = +15.4°$ (1 molar solution in chloroform; cell length of 10 cm).

The substances listed in the following examples are obtained in an analogous manner:

Example 5

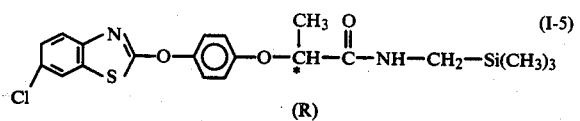

Melting point: 88° C.

Optical rotation $[\alpha]_D^{24} = +6.7°$ (1 molar solution in chloroform; cell length of 10 cm).

Example 6

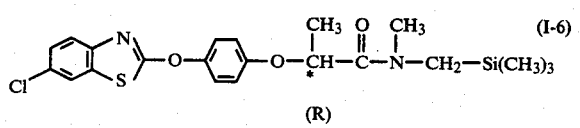

Melting point: 70° C.

Optical rotation $[\alpha]_D^{24} = +7.3°$ (1 molar solution in chloroform; cell length of 10 cm).

Example 7

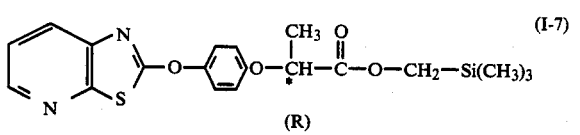

A solution of 10.7 g (0.05 mole) of 2-methylsulphonyl-thiazol[5,4-b]pyridine in 30 ml of dimethylsulphoxide is slowly added dropwise to a mixture of 13.4 g (0.05 mole) of the R-enantiomer of trimethylsilyl-methyl 2-(4-hydroxy-phenoxy)-propionate, 1.85 g (0.025 mole) of calcium hydroxide and 20 ml of dimethylsulphoxide at 40° C., with stirring. The mixture is subsequently stirred at 40° C. for 2 hours and at room temperature for 16 hours. Working up is then carried out by a procedure in which the reaction mixture is poured into water, the oily product obtained is extracted with chloroform and the organic phase is washed rapidly in each case once with 5% strength aqueous sodium hydroxide solution, dilute acetic acid and water and, after drying, is concentrated by stripping off the diluent under reduced pressure. 19 (94.5% of theory) of the R-enantiomer of the compound of the abovementioned formula (I-7) are obtained in this manner.

Refractive index: $n_D^{25} = 1.5530$.

PREPARATION OF STARTING SUBSTANCES

Example (VII-1)

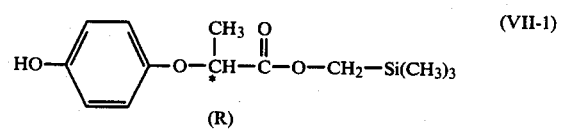

206 g (0.57 mole) of the R-enantiomer of (trimethylsilyl-methyl) 2-[4-(benzyloxyphenoxy)]-propionate are dissolved in 1,200 ml of ethyl acetate and hydrogenated in the presence of 40 g of palladium on active charcoal (5%) of temperatures of 40° to 60° C. with hydrogen under a pressure of 60 bar. Working up is then carried out by a procedure in which the catalyst is filtered off and the filtrate is concentrated by stripping off the diluent under reduced pressure. 150 g (98% of theory) of the R-enantiomer of trimethylsilyl-methyl 2-(4-hydroxy-phenoxy)-propionate are obtained in this manner.

Refractive index: $n_D^{24} = 1.4983$

Optical rotation: $[\alpha]_D^{24} = +6.64°$ (1 molar solution in chloroform; cell length of 10 cm).

The substances listed in the following Table 2 can also be prepared by the method described in Example (VII-1):

TABLE 2

| Example No. | Y | R² |
|---|---|---|
| VII-2 | O | C₂H₅ |
| VII-3 | O | n-C₃H₇ |
| VII-4 | O | n-C₄H₉ |
| VII-5 | NH | CH₃ |
| VII-6 | NH | C₂H₅ |
| VII-7 | NH | n-C₃H₇ |
| VII-8 | NH | n-C₄H₉ |
| VII-9 | NCH₃ | CH₃ |
| VII-10 | NCH₃ | C₂H₅ |
| VII-11 | NCH₃ | n-C₃H₇ |
| VII-12 | NCH₃ | n-C₄H₉ |
| VII-13 | S | CH₃ |
| VII-14 | S | C₂H₅ |
| VII-15 | S | n-C₃H₇ |
| VII-16 | S | n-C₄H₉ |

Example (VIII-1)

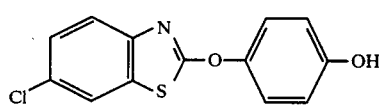
(VIII-1)

A mixture of 11 g (0.1 mole) of hydroquinone, 50 ml of dimethylsulphoxide and 3.7 g (0.05 mole) of calcium hydroxide is heated to 80° C., under nitrogen. A solution of 10.2 g (0.05 mole) of 2,6-dichlorobenzothiazole in 10 ml of dimethylsulphoxide is then slowly added dropwise at this temperature, with stirring. The mixture is subsequently stirred at 80° C. for 8 hours. Working up is then carried out by a procedure in which the reaction mixture is concentrated by stripping off the solvent, water and aqueous hydrochloric acid are added to the residue which remains and the solid product which precipitates is filtered off with suction and dried. 11.1 g (80% of theory) of 4-(6-chloro-2-benzothiazolyl)-oxyphenol are obtained in this manner.

Melting point: 174° C. (after recrystallization from xylene).

Example (VIII-2)

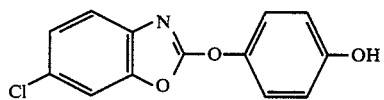
(VIII-2)

The compound of the formula (VIII-2) is also prepared by the method described in Example (VIII-1).
Yield: 85% of theory
Melting point: 176° C. (after recrystallization from butanol).

Example (XII-1)

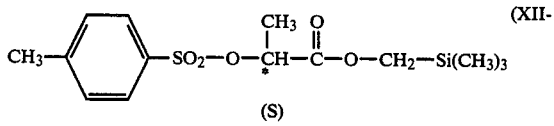
(XII-1)
(S)

33 g (0.41 mole) of pyridine are slowly added dropwise to a mixture of 109 g (0.41 mole) of the S-enantiomer of tosyloxy-propionic acid chloride, 43.4 g (0.41 mole) of trimethylsilyl-methanol and 250 ml of toluene at 20° C., with stirring. The mixture is subsequently stirred at room temperature for 24 hours. Working up is then carried out by a procedure in which the reaction mixture is poured into water and extracted with toluene and the organic phase is concentrated by stripping off the diluent under reduced pressure. 130 g (96% of theory) of the S-enantiomer of trimethylsilyl-methyl 2-tosyloxy-propionate are obtained in this manner in the form of an oily product.

Boiling point: 145°–155° C./0.05 mbar.

The substances listed in the following Table 3 can also be prepared by the method described in Example (XII-1):

TABLE 3

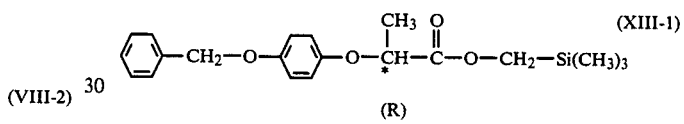
(XIIa)

| Example No. | Y | $R^2$ |
|---|---|---|
| XII-2 | O | $C_2H_5$ |
| XII-3 | O | n-$C_3H_7$ |
| XII-4 | O | n-$C_4H_9$ |
| XII-5 | NH | $CH_3$ |
| XII-6 | NH | $C_2H_5$ |
| XII-7 | NH | n-$C_3H_7$ |
| XII-8 | NH | n-$C_4H_9$ |
| XII-9 | $NCH_3$ | $CH_3$ |
| XII-10 | $NCH_3$ | $C_2H_5$ |
| XII-11 | $NCH_3$ | n-$C_3H_7$ |
| XII-12 | $NCH_3$ | n-$C_4H_9$ |
| XII-13 | S | $CH_3$ |
| XII-14 | S | $C_2H_5$ |
| XII-15 | S | n-$C_3H_7$ |
| XII-16 | S | n-$C_4H_9$ |

Example (XIII-1)

$$\text{Ph—CH}_2\text{—O—C}_6\text{H}_4\text{—O—CH(CH}_3\text{)—C(=O)—O—CH}_2\text{—Si(CH}_3\text{)}_3$$ (XIII-1)
(R)

A mixture of 100 g (0.5 mole) of hydroquinone monobenzyl ether, 165 g (0.5 mole) of the S-enantiomer of trimethylsilyl-methyl 2-tosyloxypropionate, 1,000 ml of methyl iso-butyl ketone and 138 g (1 mole) of potassium carbonate is stirred at 85°–90° C. for 5 hours. Working up is then carried out by a procedure in which the solid residue is filtered off with suction, the solvent is distilled off, the residue which remains is dissolved in 800 ml of toluene and the organic phase is washed twice with 1,000 ml of 5% strength aqueous sodium hydroxide solution each time at 40° C., then rendered acid with a little glacial acetic acid and washed neutral with water. After the solvent has been stripped off under reduced pressure, 107 g (60% of theory) of the R-enantiomer of trimethylsilyl-methyl 2-[4-(benzyloxy-phenoxy)]-propionate are obtained in the form of an oil.

Refractive index: $n_D^{24} = 1.5216$.
Optical rotation: $[\alpha]_D^{24} = +7.31°$ (1 molar solution in chloroform; cell length of 10 cm).

The substances listed in the following Table 4 can also be prepared by the method described in Example (XIII-1):

TABLE 4

(XIII)

| Example No. | Y | $R^2$ |
|---|---|---|
| XIII-2 | O | $C_2H_5$ |
| XIII-3 | O | n-$C_3H_7$ |
| XIII-4 | O | n-$C_4H_9$ |
| XIII-5 | NH | $CH_3$ |
| XIII-6 | NH | $C_2H_5$ |

TABLE 4-continued

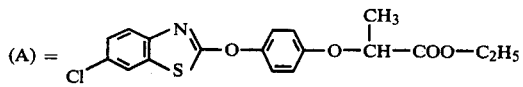
(XIII)

| Example No. | Y | R² |
|---|---|---|
| XIII-7 | NH | n-C₃H₇ |
| XIII-8 | NH | n-C₄H₉ |
| XIII-9 | NCH₃ | CH₃ |
| XIII-10 | NCH₃ | C₂H₅ |
| XIII-11 | NCH₃ | n-C₃H₇ |
| XIII-12 | NCH₃ | n-C₄H₉ |
| XIII-13 | S | CH₃ |
| XIII-14 | S | C₂H₅ |
| XIII-15 | S | n-C₃H₇ |
| XIII-16 | S | n-C₄H₉ |

The following compound was employed as the comparison substance in the biological tests described below:

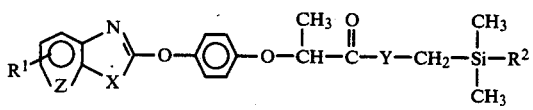

Ethyl 2-{4-[(6-chloro-2-benzothiazolyl)-oxy]-phenoxy}-propionate (known from DE-OS (German Published Specification) No. 2,640,730).

EXAMPLE A

Pre-emergence test/greenhouse

Solvent: 5 parts by weight of acetone.
Emulsifier: 1 part by weight of alkylaryl polyglycol ether.

To produce a suitable preparation of active compound, 1 part by weight of active compound is mixed with the stated amount of solvent, the stated amount of emulsifier is added and the concentrate is diluted to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, the active compound according to Example 1 exhibits a better selective herbicidal activity than comparison substance (A) when applied in an amount of 0.5 kg/ha for combating Setaria in wheat.

EXAMPLE B

Post-emergence test/greenhouse

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0% = no action (like untreated control)
100% = total destruction

In this test, the active compound according to Example 1 exhibits a better selective herbicidal activity than comparison substance (A) when used for combating Digitaria and Agropyron in sugar-beet, the active compounds according to Examples 2 and 3 exhibits in wheat a better selective herbicidal activity than comparison substance (A).

It will be understood that the specification and examples are illustrative but not limitative of the present invention and that other embodiments within the spirit and scope of the invention will suggest themselves to those skilled in the art.

We claim:

1. A phenoxypropionic acid derivative of the formula

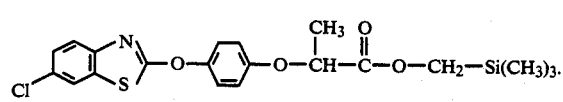

in which
X represents oxygen or sulphur,
Y represents oxygen, sulphur or the grouping of the formula NR,
R represents hydrogen or alkyl with 1 to 6 carbon atoms,
Z represents nitrogen or the CH group,
R¹ represents hydrogen or halogen and
R² represents alkyl with 1 to 6 carbon atoms.

2. A phenoxypropionic acid derivative according to claim 1, in which
R represents hydrogen or alkyl with 1 to 4 carbon atoms,
R¹ represents hydrogen, fluorine, chlorine or bromine and
R² represents alkyl with 1 to 4 carbon atoms.

3. A phenoxypropionic acid derivative according to claim 1, in which the phenoxypropionic acid derivative is an R-enantiomer.

4. A phenoxypropionic acid derivative according to claim 1, wherein such compound is trimethylsilylmethyl 2-{4-[(6-chloro-2-benzothiazolyl)-oxy]-phenoxy}-propionate of the formula 5. A phenoxypropionic acid derivative according to claim 1, wherein such compound is trimethylsilylmethyl 2-{4-[(6-chloro-2-benzoxazolyl)-oxy]-phenoxy}-propionate of the formula

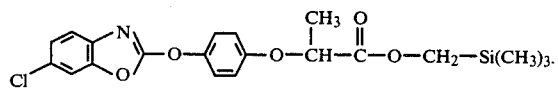

6. A phenoxypropionic acid derivative according to claim 1, wherein such compound is trimethylsilyl-methyl 2-{4-[5-chloro-2-benzoxazolyl)-oxy]-phenoxy}-propionate of the formula

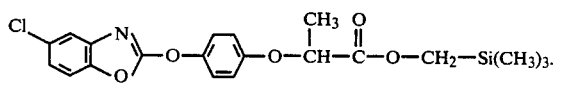

7. A phenoxypropionic acid derivative according to claim 1, wherein such compound is trimethylsilyl-methyl 2-{4-[(6-chloro-2-benzothiazolyl)-oxy]-phenoxy}-thiopropionate of the formula

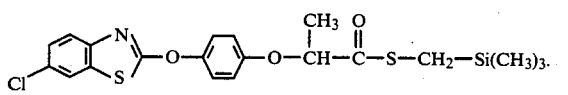

8. A phenoxypropionic acid derivative according to claim 1, wherein such compound is N-methyl-N-trimethylsilylmethyl 2-{[4-[(6-chloro-2-benzthiazolyl)-oxy]-phenoxy}-propionic acid amide of the formula

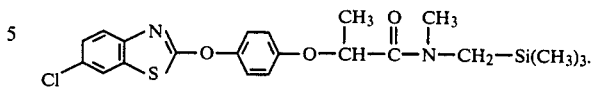

9. A herbicidal composition comprising a herbicidally effective amount of a compound according to claim 1 in admixture with a diluent.

10. A method of combating unwanted vegetation which comprises applying to such vegetation or to a locus from which it is desired to exclude such vegetation a herbicidally effective amount of a compound according to claim 1.

11. The method according to claim 10, wherein such compound is trimethylsilyl-methyl 2-{4-[(6-chloro-2-benzothiazolyl)-oxy]-phenoxy}-propionate,
trimethylsilyl-methyl 2-{4-[(6-chloro-2-benzoxazolyl)-oxy]-phenoxy}-propionate,
trimethylsilyl-methyl 2-{4-[5-chloro-2-benzoxazolyl)-oxy]-phenoxy}-propionate,
trimethylsilyl-methyl 2-{4-[6-chloro-2-benzothiazolyl)-oxy]-phenoxy}-thiopropionate or
N-methyl-N-trimethylsilyl-methyl 2-{4-[(6-chloro-2-benzthiazolyl)-oxy]-phenoxy}-propionic acid amide.

* * * * *